United States Patent

Isenberg

[11] Patent Number: 5,106,654
[45] Date of Patent: Apr. 21, 1992

[54] METHOD OF FORMING A DENSE, HIGH TEMPERATURE ELECTRONICALLY CONDUCTIVE COMPOSITE LAYER ON A POROUS CERAMIC SUBSTRATE

[75] Inventor: Arnold O. Isenberg, Pittsburgh, Pa.
[73] Assignee: Westinghouse Electric Corp., Pittsburgh, Pa.
[21] Appl. No.: 555,276
[22] Filed: Jul. 20, 1990
[51] Int. Cl.$^5$ .............................................. B05D 5/12
[52] U.S. Cl. ................................. 427/115; 427/201; 427/203; 427/255; 427/255.3; 427/355; 427/376.2; 427/419.3
[58] Field of Search .......... 427/115, 203, 355, 376.2, 427/419.3, 255, 255.3, 201

[56] References Cited

U.S. PATENT DOCUMENTS

| | | | |
|---|---|---|---|
| 4,490,444 | 12/1984 | Isenberg | 429/31 |
| 4,582,766 | 4/1986 | Isenberg et al. | 429/30 |
| 4,597,170 | 7/1986 | Isenberg | 29/623.5 |
| 4,609,562 | 9/1986 | Isenberg et al. | 427/8 |
| 4,631,238 | 12/1986 | Ruka | 429/30 |
| 4,861,345 | 8/1989 | Bowker et al. | 29/623.5 |
| 5,021,304 | 6/1991 | Ruka et al. | 427/115 |

Primary Examiner—Shrive Beck
Assistant Examiner—Benjamin L. Utech
Attorney, Agent, or Firm—Daniel P. Cillo

[57] ABSTRACT

An electrochemical device, containing a solid oxide electrolyte material and an electrically conductive composite layer, has the composite layer attached by: (A) applying a layer of $LaCrO_3$, $YCrO_3$ or $LaMnO_3$ particles (32), on a portion of a porous ceramic substrate (30), (B) heating to sinter bond the particles to the substrate, (C) depositing a dense filler structure (34) between the doped particles (32), (D) shaving off the top of the particles, and (E) applying an electronically conductive layer over the particles (32) as a contact.

10 Claims, 2 Drawing Sheets

METHOD OF FORMING A DENSE, HIGH TEMPERATURE ELECTRONICALLY CONDUCTIVE COMPOSITE LAYER ON A POROUS CERAMIC SUBSTRATE

GOVERNMENT CONTRACT

The Government of the United States of America has rights in this invention pursuant to Contract No. DE-AC-2180-ET-17089, awarded by the U.S. Department of Energy.

BACKGROUND OF THE INVENTION

The present invention relates to a method of forming an electronically conductive composite layer in a device containing solid electrolyte, preferably the device is a fuel cell.

High temperature electrical devices are taught in U.S. Pat. No. 4,490,444 (Isenberg). In this type of device, typified by a combination of electrochemical cells, a porous support tube of calcia stabilized zirconia, has an air electrode cathode deposited on it. The air electrode may be made of, for example, doped oxides of the perovskite family, such as lanthanum manganite. Surrounding the major portion of the outer periphery of the air electrode is a layer of gas-tight solid electrolyte, usually yttria stabilized zirconia. A selected radial segment of the air electrode is covered by an interconnection material The interconnection material may be made of a doped lanthanum chromite film. The generally used dopant is Mg, although Ca and Sr have also been suggested.

Both the electrolyte and interconnect material are applied on top of the air electrode by vapor deposition process, at temperatures of up to 1450° C., with the suggested use of vaporized halides of zirconium and yttrium for the electrolyte, and vaporized halides of lanthanum, chromium, magnesium, calcium or strontium for the interconnection material, as taught in U.S. Pat. No. 4,609,562 (Isenberg et al.). A fuel electrode, which is applied on top of the electrolyte is also bonded to the electrolyte by vapor deposition; here, nickel particles are anchored to the electrolyte surface by the vapor deposited skeleton of electrolyte material, as taught in U.S. Pat. Nos. 4,582,766, (Isenberg et al.) and 4,597,170 (Isenberg).

U.S. Pat. No. 4,631,238 (Ruka), in an attempt to solve potential interconnection thermal expansion mismatch problems between the interconnect, electrolyte, electrode, and support materials, taught cobalt doped lanthanum chromite, preferably also doped with magnesium, for example $LaCr_{0.93}Mg_{0.03}Co_{0.04}O_3$, as a vapor deposited interconnection mat using chloride vapors of lanthanum, chromium, magnesium, and cobalt.

It has been found, however, that there are certain thermodynamic limitations in doping the interconnection from a vapor phase by a vapor deposition process between 900° C. and 1400° C. Also, the vapor pressures of the calcium chloride, strontium chloride, cobalt chloride, and barium chloride are low at vapor deposition temperatures, and the transport to the reaction zone can be a problem. Thus, magnesium is the primary dopant used for the interconnection material. However, magnesium doped lanthanum chromite, for example $La_{0.97}Mg_{0.03}CrO_3$, has a 12% to 14% thermal expansion mismatch with the air electrode and electrolyte material.

U.S. Pat. No. 4,861,345 (Bowker et al.), in a completely different approach, taught depositing particles of $LaCrO_3$, doped with Sr, Mg, Ca, Ba or Co and coated with calcium oxide or chromium oxide, on an air electrode, and then sintering at 1,400° C. Here, the metal of the surface deposit diffused into the $LaCrO_3$ structure. This process completely eliminated vapor deposition steps and the skeletal support structure.

None of the proposed solutions solve all the problems of thermal expansion mismatch, and problems associated with doping calcium, strontium, cobalt, and barium by vapor deposition, or of providing method of depositing a uniform, leakproof conductive layer on a variety of substrates in a simple and economical fashion. It is an object of this invention to solve such problems.

SUMMARY OF THE INVENTION

Accordingly, most generally, the present invention resides in a method of forming a dense, high temperature electronically conductive composite layer on a porous ceramic substrate, characterized by the steps of: (A) applying a layer of dense particles selected from the group consisting of doped $LaCrO_3$, doped $YCrO_3$ and doped $LaMnO_3$, where the dopant is an element selected from the group consisting Mg, Ca, Sr, Ba, Ce, Co, Ni, and mixtures thereof, on a portion of a first surface of a porous ceramic substrate, (B) heating the particles to sinter them to the substrate, (C) depositing a dense oxide material between and around the particles, where the particles get embedded into the dense oxide material, (D) removing any dense oxide material that was deposited on top of the embedded particles, to expose the embedded particles, and (E) applying an electronically conductive coating over at least the particles, to provide an electronically conductive layer on the exposed particles. This method can be used to make interconnections of electrochemical cells, such as fuel cells, or to fabricate mixed conducting membranes for oxygen semipermeable devices. In this instance, the dense oxide material between the particles must be an oxygen ionic conductor.

The invention also resides in a method of forming a dense, high temperature electronically conductive composite layer on an electrode structure, characterized by the steps of: (A) applying a layer of dense particles selected from the group consisting of doped $LaCrO_3$, and doped $YCrO_3$, where the dopant is an element selected from the group consisting of Mg, Ca, Sr, Ba, Ce, Co, Ni, and mixtures thereof, on a portion of a first surface of a porous electrode structure, (B) heating the particles to sinter bond them to the electrode, (C) electrochemical vapor depositing a dense skeletal structure comprising stabilized $ZrO_2$, between and around the doped particles, where the particles get embedded into the stabilized $ZrO_2$ structure as it grows thicker with time, (D) removing any stabilized $ZrO_2$ that was deposited on top of the embedded particles, to expose the embedded, doped particles, and (E) applying a high temperature electronically conductive coating over at least the doped particles, to provide an electronically conductive interconnection layer on the porous electrode structure.

The term "electrochemical vapor deposition" (EVD), as used herein, means applying metal halide vapor, comprising zirconium halide and also preferably yttrium halide, to the outer first surface of the porous substrate, and applying a source of oxygen to an inner second, opposite surface of the porous substrate, in a manner effective that oxygen atoms contact halide vapor at said first surface of the porous substrate. This allows a reaction of the oxygen with the metal halide vapor, and formation of a substantially 100% dense stabilized zirconia, preferably yttria stabilized zirconia structure, where with continued growth oxygen ions, permeate the structure to react with the halide vapor until the desired thickness is achieved. The term "electronically conductive" means conducting electrons but not substantially conducting ions.

Preferably, the substrate is a porous air electrode cathode made of doped $LaMnO_3$, in the form of a tubular structure of a solid oxide fuel cell, optionally supported by a porous, stabilized zirconia support tube. Additional steps, including applying a solid electrolyte layer over the remaining portion of the air cathode, and applying a cermet fuel electrode anode over the electrolyte, will complete formation of an electrochemical cell. A major advantage of this process is the total elimination of one vapor deposition process in the fabrication of a solid oxide fuel cell.

The invention further resides in a tubular electrochemical cell comprising: a porous oxide electrode, gas-tight solid electrolyte material surrounding the outer periphery of the porous oxide electrode including a narrow densified section where interconnection particles contact the porous oxide electrode, and a cermet electrode covering most of the electrolyte material exclusive of the densified interconnection section, characterized in that the interconnection particles are a layer of closely packed, discrete $LaCrO_3$ or $YCrO_3$ particles doped with an element selected from the group consisting of Ca, Sr, Ba, Ce, Co, Ni, and mixtures thereof, incorporated into the electrolyte material structure which comprises stabilized $ZrO_2$. The $LaCrO_3$ particles will have their top portion removed preferably by grinding, and plated with an electronic conductor.

The invention additionally resides in an oxygen semipermeable membrane, characterized in that electronically conducting particles selected from the group consisting of doped $LaCrO_3$, doped $YCrO_3$, doped $LaMnO_3$ particles, and mixtures thereof are embedded in stabilized $ZrO_2$, and the top particle surfaces are exposed to the atmosphere on both sides of the membrane. Doped $LaMnO_3$ particles can be used in this instance. This membrane can be coated on both sides with a thin layer of oxides of the Perovskite family, such as doped or undoped $LaCrO_3$, $LaMnO_3$, $CoPrO_3$, or $LaNiO_3$. This membrane can be placed on a porous support selected from the group of consisting $ZrO_2$, doped $LaMnO_3$, doped $LaCrO_3$ and their mixtures.

BRIEF DESCRIPTION OF THE DRAWINGS

In order that the invention can be more clearly understood, conventional embodiments thereof will now be described, by way of example, with reference to the accompanying drawings, in which:

FIG. 5 is a side view in section of the structure of FIG. 4, having any deposited material removed from the top of the particles, as by sanding, or the like;

DESCRIPTION OF THE PREFERRED EMBODIMENTS

Figure 1:
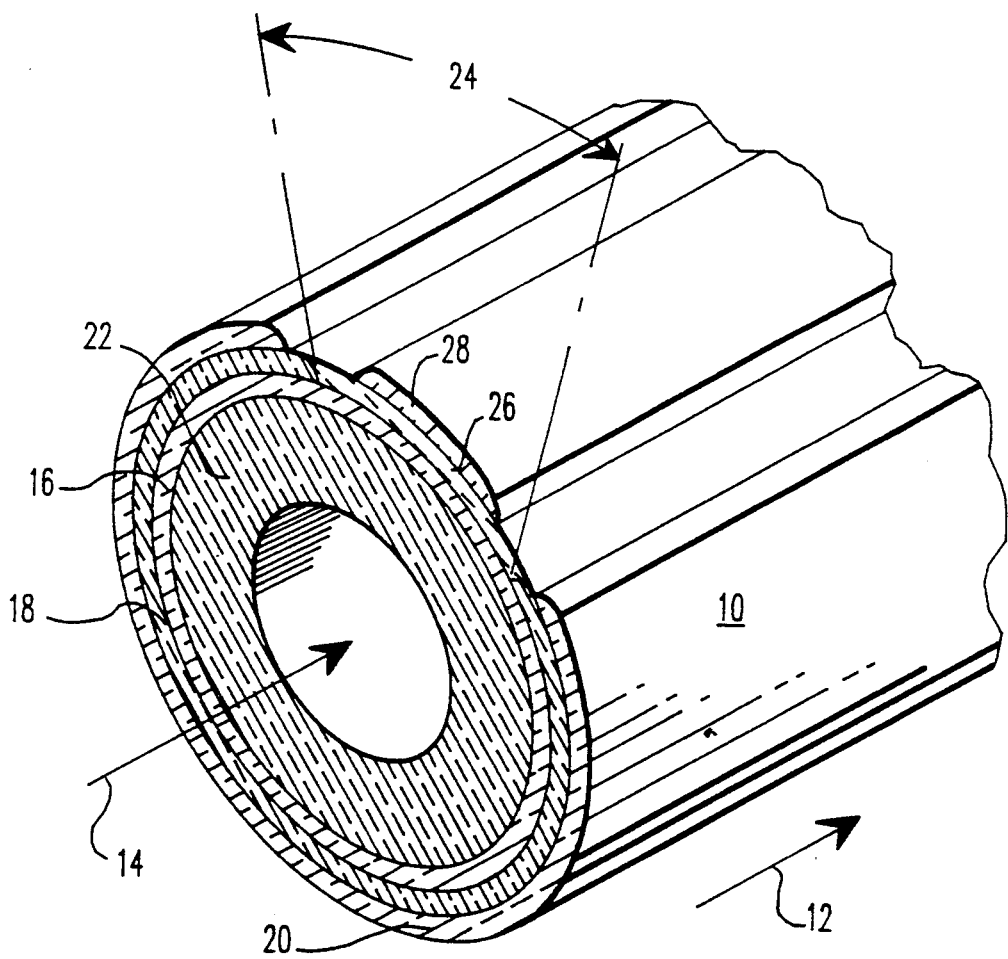
FIG. 1 is a schematic sectional view of a preferred embodiment of a single, tubular electrochemical cell, showing the interconnection layer formed by the method of this invention on top of a supporting electrode.

Referring now to FIG. 1 of the Drawings, a preferred, tubular, electrochemical cell 10 is shown. The preferred configuration is based upon a fuel cell system, wherein a flowing gaseous fuel, such as hydrogen or carbon monoxide, is directed axially over the outside of the cell, as indicated by the arrow 12, and an oxidant, such as air, or $O_2$ indicated by the arrow 14, flows through the inside of the cell. Where the cell is as shown, oxygen molecules pass through porous, electronically conductive electrode structure 16 and are changed to oxygen ions which pass through the electrolyte 18, to combine with fuel at the fuel electrode 20, which is usually of a metal-ceramic or cermet construction.

It should be noted that the following description of a preferred tubular configuration should not be considered limiting in any manner. It should also be noted that the electronically conducting composite layer of this invention, described hereinafter, could be applied to a variety of substrates and to electrochemical cells other than fuel cells, and in one instance as an example, can be used for $O_2$ separation from air, by forming a mixed conducting membrane which is permeable to oxygen at elevated temperatures. In the case of fuel cells, the term "air electrode" as used throughout means that electrode which will be in contact with oxidant, and "fuel electrode" means that electrode that will be in contact with fuel.

The invention will hereinafter be primarily described with reference to its preferred embodiment in a fuel cell. The cell 10 can include an optional, porous support tube 22. The support tube can be comprised of calcia stabilized zirconia, forming a porous wall approximately one to two millimeters thick. The air electrode, or cathode 16 is a porous, oxide structure approximately 50 micrometers to 1,500 micrometers (0.05 millimeter to 1.5 millimeter) thick. It can be deposited on the support tube by slurry dip and sinter techniques, or extruded as a self-supporting structure. The air cathode is, for example, comprised of doped oxides or mixtures of oxides of the perovskite family, such as $LaMnO_3$, $CaMnO_3$, $LaNiO_3$, $LaCoO_3$, $LaCrO_3$, and the like. Preferred dopants are Mr, Ca, Sr, Ba, Ce, Co and Ni.

Surrounding most of the outer periphery of the air electrode 16 is a layer of gas-tight solid electrolyte 18, generally comprised of yttria stabilized zirconia about 1 micrometer to about 100 micrometers thick (0.001 millimeter to 0.1 millimeter). The electrolyte 18 can be deposited onto the air electrode by well known, high temperature, electrochemical vapor deposition techniques. In the case where electrolyte is to be deposited before the interconnection, a selected radial segment or portion 24 of the air electrode 16 is masked during electrolyte deposition and then a layer of a nonporous interconnection material 26 is deposited on this segment or portion 24. If the interconnection is to be deposited first then the electrolyte portion of the air electrode is masked initially.

The dense interconnection material 26, which preferably extends the active axial length of each elongated cell 10 as shown, must be electrically conductive in both an oxidant and fuel environment. The gas-tight interconnection 26 is roughly similar in thickness to the electrolyte, about 30 micrometers to about 100 micrometers (0.03 millimeter to 0.1 millimeter). The interconnection should be non-porous (over about 95% dense) and preferably be nearly 99% to 100% electronically conductive at 1000° C., the usual operating temperature of a fuel cell.

The interconnection must be dense and leakproof and also have a coefficient of thermal expansion close to that of the solid electrolyte, and the electrode onto which it is deposited, and the other components, including the support tube, if used. The usual interconnection material is doped lanthanum chromite, of approximately 20 micrometers to 50 micrometers (0.02 millimeter to 0.05 millimeter) thickness. Usually, an electrically conductive top layer 28 is deposited over the interconnection 26. This top layer is preferably comprised of the same material as the fuel anode, that is, nickel or cobalt zirconia cermet, and is about the same thickness, 100 micrometers. Presently used lanthanum chromite interconnections, produced by EVD have an approximate 14% mismatch of thermal expansion coefficient with the rest of the fuel cell components.

This invention consists of bonding a given amount of individual particles, of desired interconnection composition, preferably by means of an EVD grown, gas tight filler. The process consists of applying these particles, in a densely packed layer onto a selected portion of a substrate, such as the air electrode surface in an amount effective to provide sufficient electronically conducting surface area to achieve a low resistance contact to the underlying oxide electrode.

The overall physical, chemical and electrical properties of such composite interconnection will be influenced by the individual properties of the particles and that of the surrounding EVD grown, stabilized $ZrO_2$ skeleton. For example, a deposit of $LaCrO_3$ particles doped with at least one of Mg, Ca, Sr, Ba, Ce, Co, and Ni, could be deposited and pressed into the interconnection site and then stabilized $ZrO_2$ film grown in between and around the particles by EVD. The packing density and shape of the particles is best characterized by close-packed spheres in its preferred embodiment The chemical stability, thermal expansion and electronic conductivity of the composite interconnection is determined by the level of doping of the lanthanum chromite particles.

Figure 2:
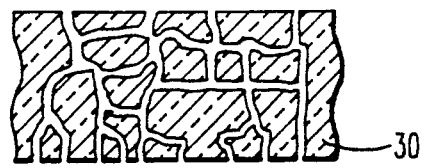
FIG. 2 is a side view in section of a substrate, which can be either an air electrode or a simple support structure.

FIG. 2 shows a bare section of porous ceramic substrate 30, which can be the porous air electrode material described previously, such as $LaMnO_3$ doped with Sr, for fuel cell application, or a porous support material, such as calcia stabilized zirconia, for example $(ZrO_2)_{0.85}(CaO)_{0.15}$ where an $O_2$ separation device is to be constructed. The substrate could be presintered, or could be "green", that is unsintered, or have a top "green" layer supported by a sintered support, so that particles can easily be pressed into or otherwise applied its top surface.

Figure 3:
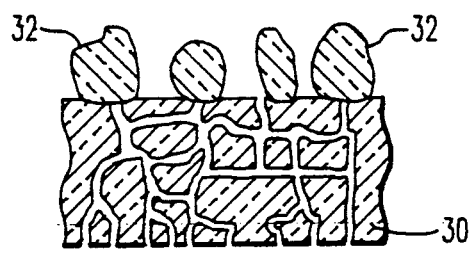
FIG. 3 is a side view in section of the substrate of FIG. 2 having particles applied to it.

FIG. 3 shows a layer, preferably a closely packed layer of particles 32 applied to the unsintered substrate 30. The particles can be, for example, sieved over the substrate and then pressed into place. Wetting the substrate with water or other liquids, or a slurry of fine $LaMnO_3$ powder before particle application helps adherence. Of course, other methods of applying a closely packed layer of particles can be used, for example tape application. The particles preferably approach a circular cross-section, and would be selected from the group consisting of $LaCrO_3$, $YCrO_3$, and mixtures thereof, each doped with an element selected from Mg, Ca, Sr, Ba, Ce, Co, Ni, and their mixtures. $LaCrO_3$ doped with cerium and calcium is preferred, especially for fuel cell applications.

Figure 4:
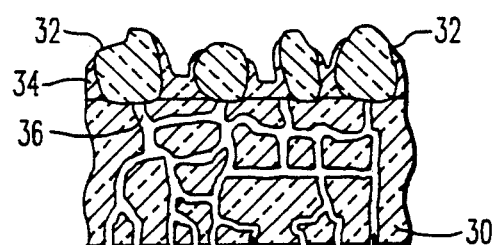
FIG. 4 is a side view in section of the applied particles shown in FIG. 3, with deposited material between them.

The weight of doped particles 32 will constitute from approximately 5 weight % to 99 weight %, preferably from 90 wt % to 99 wt % in the case of electrochemical cells, of the composite electronically conductive layer shown in FIG. 4, that is, particles 32 plus deposited stabilized $ZrO_2$ filler material 34. The doped particles 32 will have diameters from approximately 75 micrometers to 1,000 micrometers, preferably about 400 micrometers to 600 micrometers. The particles will cover from 5% to 99% of the surface area on the portion of the surface where they are deposited. These particles must be of sufficient size so that the grinding step shown in FIG. 5 can be accomplished without creating porosity in the composite structure.

In instances where an $O_2$ separation device is to be constructed, a bed of smaller powder particles (not shown) of the same or similar composition as particles 32, except that $LaMnO_3$ doped with the same materials as the other particles can also be used, can be laid down first over a substrate of calcia stabilized zirconia or the like. Then the larger particles 32 can be pressed into place. After applying particles 32, they are heated, along with the substrate at between approximately 1,250° C. and 1,450° C. to sinter them to the substrate, ensuring good particle bonding and also sintering of the "green" portion of the substrate structure.

In FIG. 4, a dense skeletal structure material 34, preferably comprising stabilized $ZrO_2$, most preferably yttria stabilized zirconia, for example $(ZrO_2)_{0.9}(Y_2O_3)_{0.1}$ is deposited between the particles 32 deposition can be accomplished preferably, by electrochemical vapor deposition (EVD), generally following the method of U.S. Pat. No. 4,609,562 herein incorporated by reference. This application of stabilized $ZrO_2$ embeds the particles 32 into the dense filler structure material 34 as the filler grows thicker with time and closes the pores 36 in the support 30.

The dense stabilized zirconia material 34 is nearly 100% dense. This stabilized zirconia material 34 can and in many cases will cover a major portion of the tops of the particles 32, as shown, forming, in some instances, an electronically insulating coating over the particles, since stabilized $ZrO_2$ is ionically, not electronically conducting. This material should be removed in order to accomplish electronic contact through the chromite particles to the underlying oxide electrode. In some instances a melt impregnation deposit of a gas impervious, electrical insulator, such as recrystallizing glasses on silicate basis can be substituted for the vapor deposited stabilized $ZrO_2$. In this case, oxygen transfer cannot be accomplished across such a composite layer for semipermeable oxygen membranes.

Figure 5:
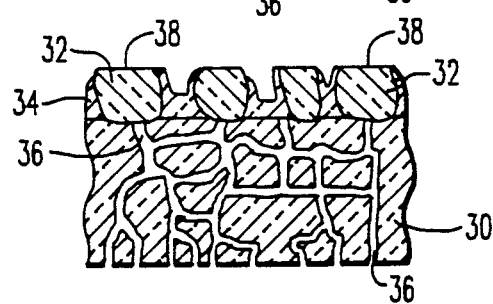

FIG. 5 shows removal of any stabilized $ZrO_2$ that was deposited or formed on top of the embedded particles 32. As can be seen, the tops of the embedded particles 32 have been shaved (ground) off, leaving a flat, top, electronically conducting particle surface 38 free of stabilized $ZrO_2$ material 34. As can be seen, the stabilized zirconia 34 partly fills the deep valleys between the particles 32. This step can be accomplished using a fine grit belt grinder, or other abrasive techniques. The grinding attacks only the high particle spots and not the main body of the layer on the substrate, leaving the layer gas tight.

Figure 6:
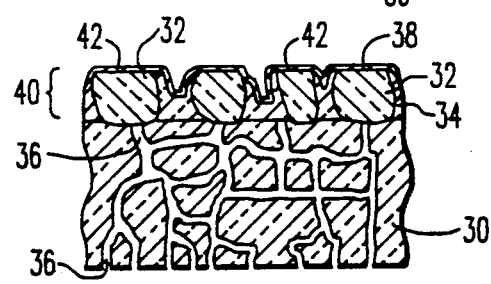
FIG. 6, which best shows the invention, is a side view in section of the structure of FIG. 5, having an electronically conductive coating applied over at least the particles, and as shown here, also the skeletal structure.

FIG. 6 shows a composite layer 40 on the support 30. Here an electronically conductive layer 42, approximately 0.01 micrometer to 1 micrometer thick, preferably 0.1 micrometer to 0.5 micrometer thick, is applied over the entire surface 38 of the particles 32 and the filler 34. This layer 42 is optional. It is applied only to block oxygen ion migration through the stabilized $ZrO_2$ material 34, and to minimize electrochemical "short currents", if this is seen as a problem, in the case of a fuel cell. In the case of a melt impregnated, gas impermeable insulator as filler material 34, as described previously, layer 42 is not required.

In the case of a fuel cell, the layer 42 would be very thin, that is less than 1 micrometer, greater than approximately 98% dense, and consist of, for example, chromic oxide ($Cr_2O_3$), or various chromium spinels, that is materials of the $MgCr_2O_4$ type, and the like, applied by sol-gel or other techniques. As can be seen, the much larger particles 34 will substantially protrude from the coated base material 34 and allow ease of subsequent metal plating. As described previously, the plating can be directly on surfaces without intermediate film 42.

In the case of a high temperature, $O_2$ semipermeable membrane, the electronically conductive layer 42 must be permeable to oxygen and can comprise fine, closely packed, sintered $LaCrO_3$ or $YCrO_3$ particles. In this instance, as described previously, a similar layer could be placed as a bed on top of the support 30, as a first step, before applying large particles 32.

If an electronically conducting oxide is used as a porous support, for example, a self-supporting air electrode, the bed layer described above could be eliminated. In this arrangement, oxygen from one side of the membrane pass as ions through the stabilized zirconia, if a concentration gradient exists across the membrane. Electrons would travel along the bed of fine $LaCrO_3$ or $YCrO_3$ particles on the support, through the large $LaCrO_3$ or $YCrO_3$ particles 32, and along the thin top layer of $LaCrO_3$ or $YCrO_3$ particles 42. For instance, pressurized oxygen gas on one side of the membrane plus the electrons would form oxygen ions which would pass through the stabilized zirconia acting as solid electrolyte. This would provide a short circuit effect allowing $O_2$ separation without application of an external current source, however, this can take place only at elevated temperatures when oxygen ion mobility is increased.

Figure 7:
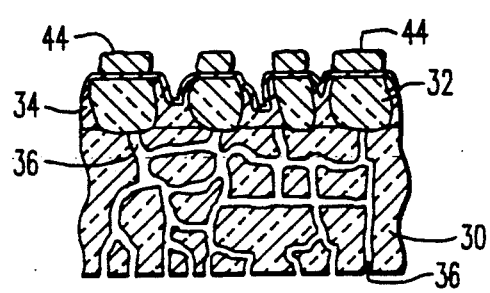
FIG. 7 is a side view in section of the composite structure of FIG. 6, with a variety of further plating coatings.

FIG. 7 shows a separate metal plating current collector section 44, over top of the particles and also over layer 42. The large electronically conductive particles 32 are prominently exposed, and plating will primarily cover their top surfaces 38, as shown. The plating thickness usually ranges from about 15 micrometers to 50 micrometers. These sections 44, would be used primarily for fuel cell applications. As described previously, electronically conductive layer 42 can substitute for plating layer 44, since layer 42 need only be applied over the particles 32. Also, electronically conductive layer 42 could be eliminated since it is optional. In any case, a high temperature, electronically conductive coating will be applied over at least the particles 32. The metal plating layer will preferably contain nickel The interconnection islands or sections 44 can all be then connected with thin nickel foil (not shown), which would be a contacting surface for cell-to-cell interconnection.

The invention will now be illustrated with reference to the following Example.

EXAMPLE

A tubular structure having the components shown in FIG. 1 was constructed. A sintered lanthanum manganite ($La_{0.84}Sr_{0.16}MnO_3$), air electrode structure was sprayed with a water slurry of fine $La_{0.84}Sr_{0.16}MnO_3$ powder (1 micrometer to 5 micrometer particles), approximately 100 micrometers in thickness, over a radially masked segment of the air electrode, shown as 24 in FIG. 1. The air electrode was approximately 1,000 micrometers (1.0 millimeter) thick. The interconnection site area was approximately 0.9 cm wide $\times$ 30.5 cm long. Then, doped lanthanum chromite particles, $La_{0.84}Sr_{0.16}CrO_3$ particles about 500 micrometers in diameter, were applied by sieving onto the wet lanthanum manganite slurry coating, covering coating, covering over 50% of the surface area. There was no heating up to this point. Then the particle containing cell tube was dried and heated at 1,400° C. for 1 hour to sinter bond the doped $LaCrO_3$ particles to the tube.

The porous tubular structure was then loaded into an evacuated vapor deposition (EVD) apparatus and heated up to 1,200° C. At temperature, oxygen plus steam was fed through the tube inside, so that oxygen would diffuse to the surface of the air electrode. Vapors of zirconium chloride, and yttrium chloride were then fed to contact the tube outside, the doped lanthanum chromite particles, and the air electrode structure, using a process based on that taught in U.S. Pat. No. 4,609,562.

The oxygen and metal halide vapors started to react at the air electrode top surface, forming a yttrium doped zirconia, $[(ZrO_2)_{0.9}(Y_2O_3)_{0.1}]$ filler on the air electrode, in between and bonding tightly to the $La_{0.84}Sr_{0.16}CrO_3$ particles. As the reaction continued, the filler layer grew in thickness, incorporating the particles. The vapor deposition reaction was discontinued after approximately 1 hour, providing a non-porous, stabilized zirconia electrolyte film over the air electrode and simultaneously providing gas tightness to and forming the composite interconnection, such as shown schematically in FIG. 4 of the drawings. Then a nickel-zirconia cermet fuel electrode was fixed by standard techniques onto the electrolyte, as taught in U.S. Pat. No. 4,597,170.

The top surface of the interconnection layer was then sanded with a 400 grit diamond sanding pad until it appeared somewhat similar to the cross-section shown in FIG. 5 of the drawings. The doped lanthanum chromite particles were sanded such that flat, top sections were exposed and excess stabilized zirconia was removed. After sanding, a thin, oxygen ion blocking layer, about 0.1 micrometer thick, of chromium oxide was applied by painting the surface with a chromium (III)-nitrate-saturated-methanol solution. The coating was dried and thermally decomposed at 500° C. in air, leaving a thin $Cr_2O_3$ layer over the contact surface. The surface of the interconnection particles was then plated with nickel from a nickel acetate bath, to provide a cross-section somewhat similar to FIG. 7 of the drawings. This processing sequence provides a dense, high temperature electronically conductive composite layer onto the porous ceramic air electrode substrate.

Resistance for the test cell utilizing the 500 micron interconnection particles in the composite interconnection layer at 1,000° C. was 0.64 $\Omega cm^2$. This compares favorably with standard fuel cells, containing all electrochemical vapor deposited interconnection material, and having resistance values of 0.50 $\Omega cm^2$ at 1,000° C. The test cell, having an active area of 127 $cm^2$ was operated at 1,000° C. with hydrogen and 3% $H_2O$ as fuel for 168 hours. The current was maintained at 31.7 A (250 $mA/cm^2$) and a fuel utilization of 85% was established. The cell open circuit voltage at the established gas flow was 1,015 mV to 1,018 mV (1,070 mV was expected), indicating only minor porosity composite interconnection which was due to some porosity in the chromite particles After the test, microscopic topographical inspection did not show any abnormal alteration of the interconnection features.

A semipermeable oxygen membrane could be made with minor modifications to the method just described, where calcia stabilized zirconia would be substituted for the air electrode material and where a thin porous layer of very fine, doped lanthanum chromite particles or other conductive oxides would be laid down as a first layer with subsequent application of the composite layer of stabilized zirconia plus the chromite particles. Such a structure is permeable to oxygen if a concentration gradient exists across such a membrane. However, the packing density of chromite particles is adjusted to optimize the oxygen permeability, not the electronic conduction, that is, the packing density of the chromite particles is reduced to a level so that the electronic resistance does not become the limiting membrane resistance.

If an oxygen semipermeable membrane operates at elevated oxygen activities on both sides, other mixed oxides that are not stable in reducing gas atmospheres can be used as granules or particles. Such materials would be similar to oxides that are used for air electrodes of fuel cells, such as doped lanthanum manganite ($LaMnO_3$).

I claim:

1. A method of forming a dense, high temperature electronically conductive composite layer on a porous ceramic substrate comprising the steps
   (A) applying a layer of dense particles selected from the group consisting of doped $LaCrO_3$, doped $YCrO_3$ and doped $LaMnO_3$, where the dopant is an element selected from the group consisting of Mg, Ca, Sr, Ba, Ce, Co, Ni, and mixtures thereof, on a portion of a first surface of a porous ceramic substrate,
   (B) heating the particles to sinter them to the substrate,
   (C) depositing a dense oxide material between and around the particles, where the particles get embedded into the dense oxide material,
   (D) removing any dense oxide material that was deposited on top of the embedded particles, to expose the embedded particles, and
   (E) applying an electronically conductive coating over at least the particles, to provide an electronically conductive layer on the exposed particles.

2. The method of claim 1, where the doped particles cover 5% to 99% of the surface area on the portion of the surface where they are deposited, and the particles have diameters from 75 micrometers to 600 micrometers.

3. The method of claim 1, where the particles applied in step (A) are doped $LaCrO_3$ particles, the porous ceramic substrate is a doped lanthanum manganite air electrode of a solid oxide fuel cell, the dense oxide material comprises stabilized $ZrO_2$, and the deposition in step (C) is by electrochemical vapor deposition.

4. The method of claim 1, where a fine layer of particles selected from the group consisting of $LaCrO_3$, $YCrO_3$, and $LaMnO_3$, each doped with an element selected from the group consisting of Mg, Ca, Sr, Ba, Ce, Co, Ni, and mixtures thereof, said particles having a smaller diameter than the particles applied in step (A), is deposited, as a first step, on the portion of the first surface of the porous ceramic substrate, and also as the conductive coating of step (E), and where the ceramic substrate is made of stabilized zirconia.

5. A method of forming a dense, high temperature electronically conductive composite layer on an electrode structure, comprising the steps:
   (A) applying a thin layer of dense particles selected from the group consisting of doped $LaCrO_3$ and doped $YCrO_3$ where the dopant is an element selected from the group consisting of Mg, Ca, Sr, Ba, Ce, Co, Ni, and mixtures thereof, on a portion of a first surface of a porous electrode structure,
   (b) heating the particles to sinter bond them to the electrode,
   (C) electrochemical vapor depositing a dense skeletal structure comprising stabilized $ZrO_2$, between and around the doped particles, where the particles get embedded into the stabilized $ZrO_2$ structure as it grows thicker with time,
   (D) removing any stabilized $ZrO_2$ that was deposited on top of the embedded particles, to expose the doped particles, and
   (E) applying a high temperature electronically conductive coating over at least the doped particles.

6. The method of claim 5, where the electrochemical vapor deposition step comprises heating the electrode structure, and applying metal halide vapor comprising zirconium halide and yttrium halide to the outer first surface of the porous electrode structure and applying a source of oxygen to an inner second, opposite surface of the porous electrode structure, so that oxygen contacts the metal halide vapor at said first surface of the electrode to cause a reaction of the oxygen with the metal halide vapor and cause a dense, zirconium-yttrium, oxide structure to grow from the first electrode surface, between and around the doped particles.

7. The method of claim 5, where the electrode structure is a porous, tubular, solid oxide fuel cell air electrode structure comprising doped $LaMnO_3$.

8. The method of claim 5, where the doped $LaCrO_3$ particles cover 5% to 99% of the surface area on the portion of the surface where they are deposited, and where the particles are close-packed.

9. The method of claim 5, where the doped $LaCrO_3$ particles have diameters from 75 micrometers to 1,000 micrometers, are applied as a closely packed single particle layer, and the particles remain intact within the interconnection layer in discrete form after step (B).

10. The method of claim 5, where the doped $LaCrO_3$ particles have diameters from 400 micrometers to 600 micrometers, the electrode structure is an air electrode, the particles are doped $LaCrO_3$ particles, and the layer of doped $LaCrO_3$ particles is applied in step (A) by tape application.

* * * * *